United States Patent
Buelna et al.

(10) Patent No.: US 6,719,766 B1
(45) Date of Patent: Apr. 13, 2004

(54) SURGICAL CLAMP PADS HAVING SURFACE OVERLAY

(75) Inventors: Terrence Buelna, San Francisco, CA (US); Adam Gold, Sunnyvale, CA (US); Phillip Pesta, Saratoga, CA (US); John Orlando, San Jose, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 109 days.

(21) Appl. No.: 09/645,458

(22) Filed: Aug. 24, 2000

(51) Int. Cl.[7] .............................................. A61B 17/08
(52) U.S. Cl. ....................... 606/151; 606/158
(58) Field of Search ................. 606/157, 158, 606/151, 153, 206, 205, 207, 208, 209, 210

(56) References Cited

U.S. PATENT DOCUMENTS

| | | |
|---|---|---|
| 2,743,726 A | 5/1956 | Grieshaber |
| 3,503,396 A | 3/1970 | Pierie et al. |
| 3,503,397 A | 3/1970 | Fogarty et al. |
| 3,503,398 A | 3/1970 | Fogarty et al. |
| 3,663,973 A | 5/1972 | Spence |
| 3,719,963 A | 3/1973 | Bullock, Jr. |
| 3,746,002 A | 7/1973 | Haller |
| 3,880,166 A | 4/1975 | Fogarty |
| 3,882,855 A | 5/1975 | Schulte et al. |
| 3,993,076 A | 11/1976 | Fogarty |
| 4,548,202 A | 10/1985 | Duncan |
| 4,611,593 A | 9/1986 | Fogarty et al. |
| 4,821,719 A | 4/1989 | Fogarty |
| 4,955,897 A | 9/1990 | Ship |
| 5,036,733 A | 8/1991 | Tiholiz et al. |
| 5,171,253 A | 12/1992 | Klieman |
| 5,201,746 A * | 4/1993 | Shichman .................... 606/151 |
| 5,535,756 A | 7/1996 | Parasher |
| 5,591,182 A | 1/1997 | Johnson |
| 6,007,552 A | 12/1999 | Fogarty et al. |
| 6,228,104 B1 | 5/2001 | Fogarty et al. |

FOREIGN PATENT DOCUMENTS

| | | |
|---|---|---|
| CH | 65626 | 8/1913 |
| EP | 0 490 301 A1 | 6/1992 |
| WO | WO 98/33437 | 8/1998 |
| WO | WO 99/11179 | 3/1999 |
| WO | WO 99/30623 | 6/1999 |
| WO | WO 00/78235 | 12/2000 |

OTHER PUBLICATIONS

Applied Medical Ressources, "A–Trac Atraumatic Clamping system", product description, 2 pgs.

* cited by examiner

*Primary Examiner*—Michael J. Milano
*Assistant Examiner*—D. Jacob Davis
(74) *Attorney, Agent, or Firm*—Morrison & Foerster LLP (57) ABSTRACT

A replaceable pad or insert for attachment to the jaw of a jaw-type occlusion device. The insert includes a compliant cushion and a flexible non-compliant surface overlay secured to the cushion surface. The overlay can be metal or plastic and can further include notches along the overlay sides to increase flexibility of the overlay.

12 Claims, 6 Drawing Sheets

SURGICAL CLAMP PADS HAVING SURFACE OVERLAY

BACKGROUND OF THE INVENTION

The present invention relates generally to surgical instruments for occluding a vessel or other body conduit, and more particularly, to replaceable pads or inserts for attachment to jaw-type occlusion devices.

Instruments for occluding blood vessels and other body conduits are well known. Conventional surgical clamps or clips are often made of metal, such as stainless steel, or other similarly rigid materials. Such surgical clamps are favored for a number of reasons. They can be manufactured to have a low profile, and the overall structural rigidity of the clamps together with the non-deflectable and non-deformable gripping surfaces provides a clamp having excellent gripping properties. Gripping can be further improved by providing surface irregularities to the gripping surfaces, such as scoring the surface or otherwise including serrations, teeth, or other raised protrusions. As one such example, U.S. Pat. No. 3,515,139 to Mallina discloses surgical forceps with hard plastic inserts having spherical protuberances and complementary grooves or spherical cavities. A disadvantage, however, of such clamps is that the hard surfaces and rigidity of the clamps can cause trauma to the clamped vessel at the clamping site.

As a result, a number of atraumatic instruments have been developed for reducing trauma to a vessel during occlusion. In particular, conventional surgical clamps and clips have been adapted to include jaw surfaces containing resilient members or pads. These devices likewise have their disadvantages. For example, these devices are prone to slipping off of the clamped vessel. This can be especially problematic in situations where, due to obstructions, a vessel has been clamped with only the distal tips of the clamp jaws. In such situations, the vessel can be especially prone to slipping in the direction of the distal tips. Also, due to the deformability of such pads or members, such pads or members are prone to slipping laterally on a clamped vessel, resulting in a "scissor-like" effect where the jaws can twist off-line. In such a situation, effective clamping of the vessel is compromised.

Other attempts have thus been made to atraumatically occlude a vessel in a more secure fashion. U.S. Pat. No. 3,746,002 to Hailer discloses a vascular clamp with resilient gripping members on the jaws that are formed of a resilient material having a plurality of hard pin members embedded therein. The pin members are of a length such that when a vessel is clamped between the gripping members, the resilient material deflects to accommodate the vessel, exposing the pin members which grippingly engage the outer layer of the vessel, thus securing the vessel to the gripping member. While the Haller device is less traumatic to a vessel than other occlusion devices, it nevertheless has the disadvantage of traumatizing the outer layer of the vessel.

U.S. Pat. No. 3,503,397 to Fogarty discloses surgical clamps with jaw inserts having hard plastic teeth along the edges of the insert with a softer component along the interior of the insert. The hard teeth of this device serve to resist movement of a clamped vessel laterally of the jaw, but again do so at increased risk of trauma to the vessel. Still further attempts have been made to atraumatically occlude a vessel, such as those disclosed in PCT Publication WO 99/11179.

There thus remains a need for a surgical clamp which atraumatically occludes vessels with improved gripping capabilities while simultaneously avoiding the disadvantages previously associated with existing surgical clamps or occlusion devices.

SUMMARY OF THE INVENTION

The present invention meets these and other needs and provides for replaceable surgical clamp pads or inserts having a compliant cushion and a flexible non-compliant overlay secured onto the cushion surface for engagement with a vessel or other body tissue. Various attaching structures can be provided on the cushion for securing the pad or insert onto the clamp jaw.

In one aspect of the invention, the overlay can entirely cover the cushion surface. In another aspect of the invention, a series of notches can be provided along the sides of the overlay to increase the flexibility of the overlay. The combination of surface overlay and underlying compliant cushion results in an insert that as a whole deflects to accommodate a clamped vessel while providing surface clamping characteristics associated with conventional clamps. The deflection of the insert, which is a function of the underlying compliant cushion, reduces trauma to the clamped vessel. At the same time, the non-compliant overlay provides a non-deformable clamping surface similar to that provided by conventional rigid metal or hard plastic clamps, thereby providing gripping characteristics approximating conventional rigid metal or hard plastic clamps.

In one embodiment of the invention, the overlay can be formed of a metal, such as stainless steel. In another embodiment of the invention, the overlay can be formed of a thermoplastic.

In another aspect of the invention, the overlay itself can be provided with a textured surface having surface irregularities to provide for increased traction between the overlay and the engaged vessel or body tissue. In one such embodiment the overlay can include protrusions extending from the overlay surface. In another such embodiment, such protrusions can be in the form of a plurality of columns extending from the overlay in a direction generally perpendicular to the cushion surface. In yet another such embodiment, the surface overlay can include a multiplicity of perforations.

Methods of manufacturing the replaceable pad or inserts of the present invention are also provided.

These and other features of the invention will be even better understood by reference to the accompanying drawings and description.

DETAILED DESCRIPTION OF THE INVENTION

Figure 1:
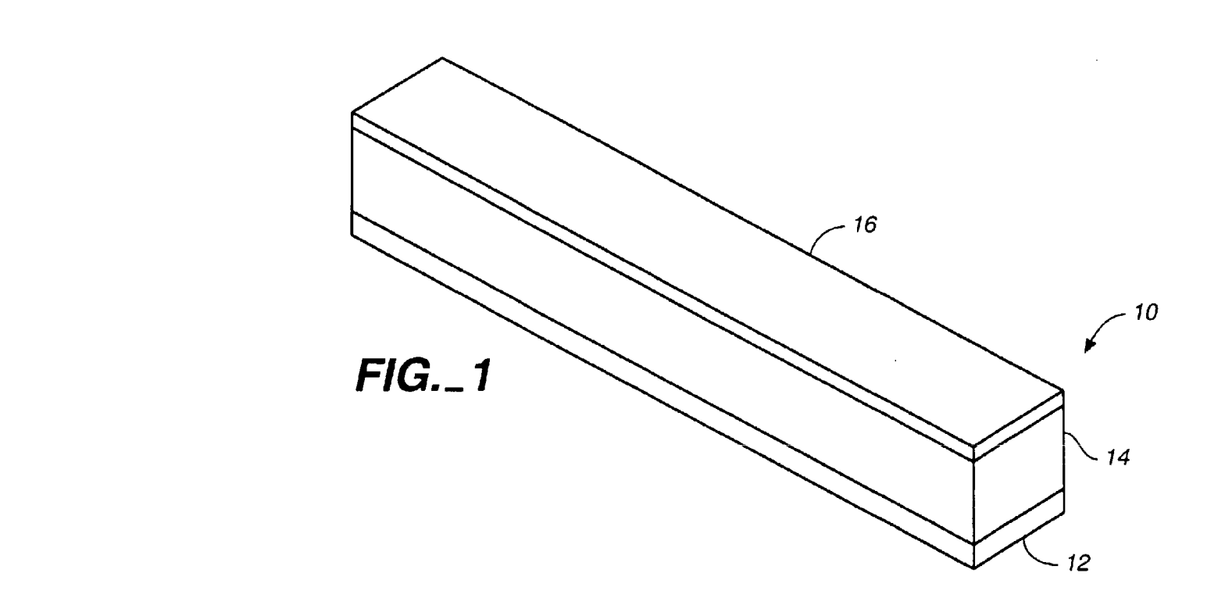
FIG. 1 is a perspective view of an insert according to a first embodiment of the invention, showing a compliant cushion with a surface overlay.
Figure 2:
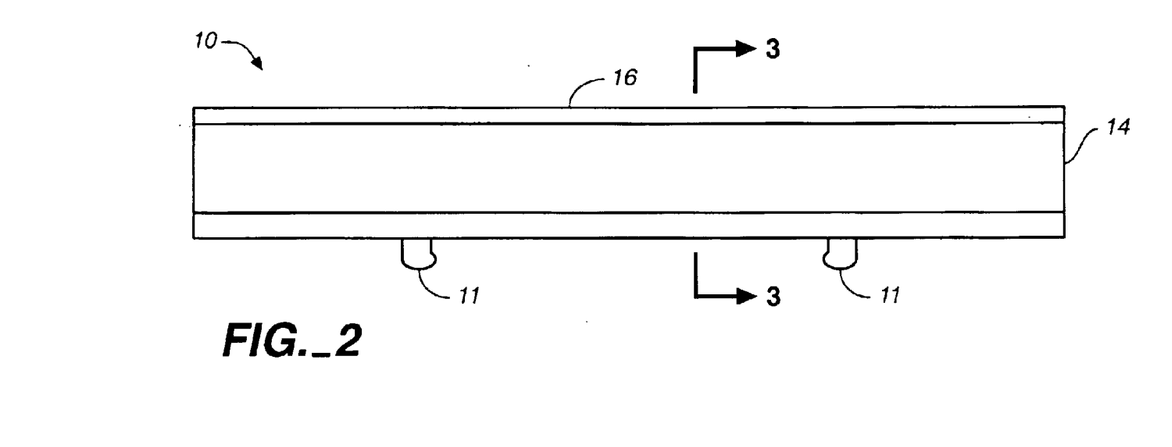
FIG. 2 is a side view of the insert of FIG. 1.
Figure 3:
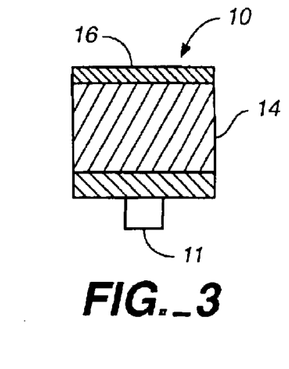
FIG. 3 is a cross-section view of the insert of FIG. 1 taken on a plane designated by line 3—3 of FIG. 2.

FIGS. 1–3 depict a first embodiment of a replaceable surgical clamp pad or insert according to the invention. Insert 10 includes cushion 14 having surface overlay 16 that extends over the cushion surface. The cushion itself is secured to attachment member 12 for attaching the insert to the jaw of a jaw-type occlusion device.

Cushion 14 can be formed of a variety of materials known in the art that are compliant and that will therefore provide a cushioning effect to a clamped vessel. Most suitable are elastomeric materials that are resiliently deflectable. Such elastomeric materials include, but are not limited to, natural rubber, neoprene, urethane, ethyl vinyl acetate foam, or silicone or silicone foam. It is desirable that the material be a thermoplastic elastomer suitable for injection molding and having a 20A–40A shore durometer rating. Such thermoplastic elastomers include polyurethane, and thermoplastic elastomers sold under the tradename KRATON™ and DYNAFLEX™ (Shell Chemicals Ltd.). The cushions of the invention can be formed in a variety of sizes and shapes. In general the cushions will conform to, or be conformable to, the jaw shape of the desired occlusion device.

Cushion 14 is secured to attachment member 12 at the surface of the cushion opposite surface overlay 16. The attachment member provides a rigid backing for the cushion as well as means for attachment of the cushion to the jaw of a clamp. Attachment member 12 can be made of a hard plastic, such as polycarbonate, or of metal. Means for attaching the attachment member to the jaw comprise a pair of protrusions 11, that can be detachably coupled to recesses on the jaw (not shown). Other conventional means of attachment may also be employed.

Figure 5A:
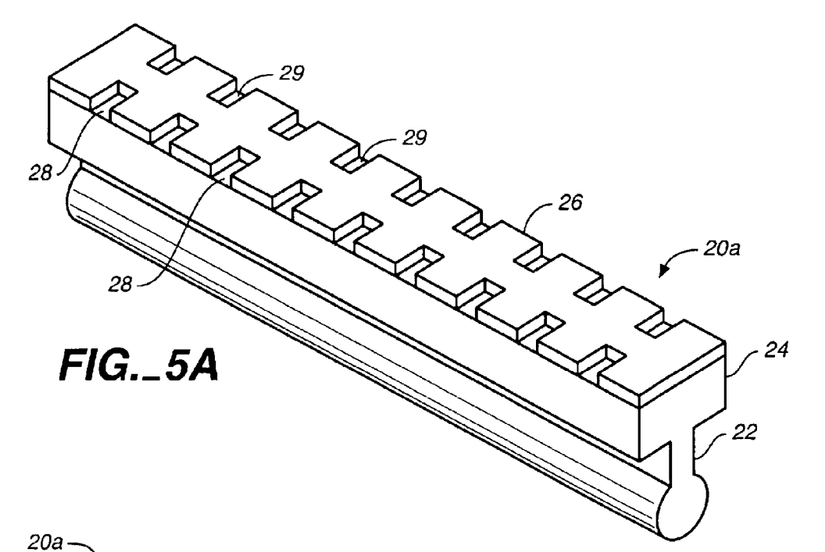
FIG. 5A is a perspective view of an insert according to a second embodiment of the invention.
Figures 5B, 5C, 7B:
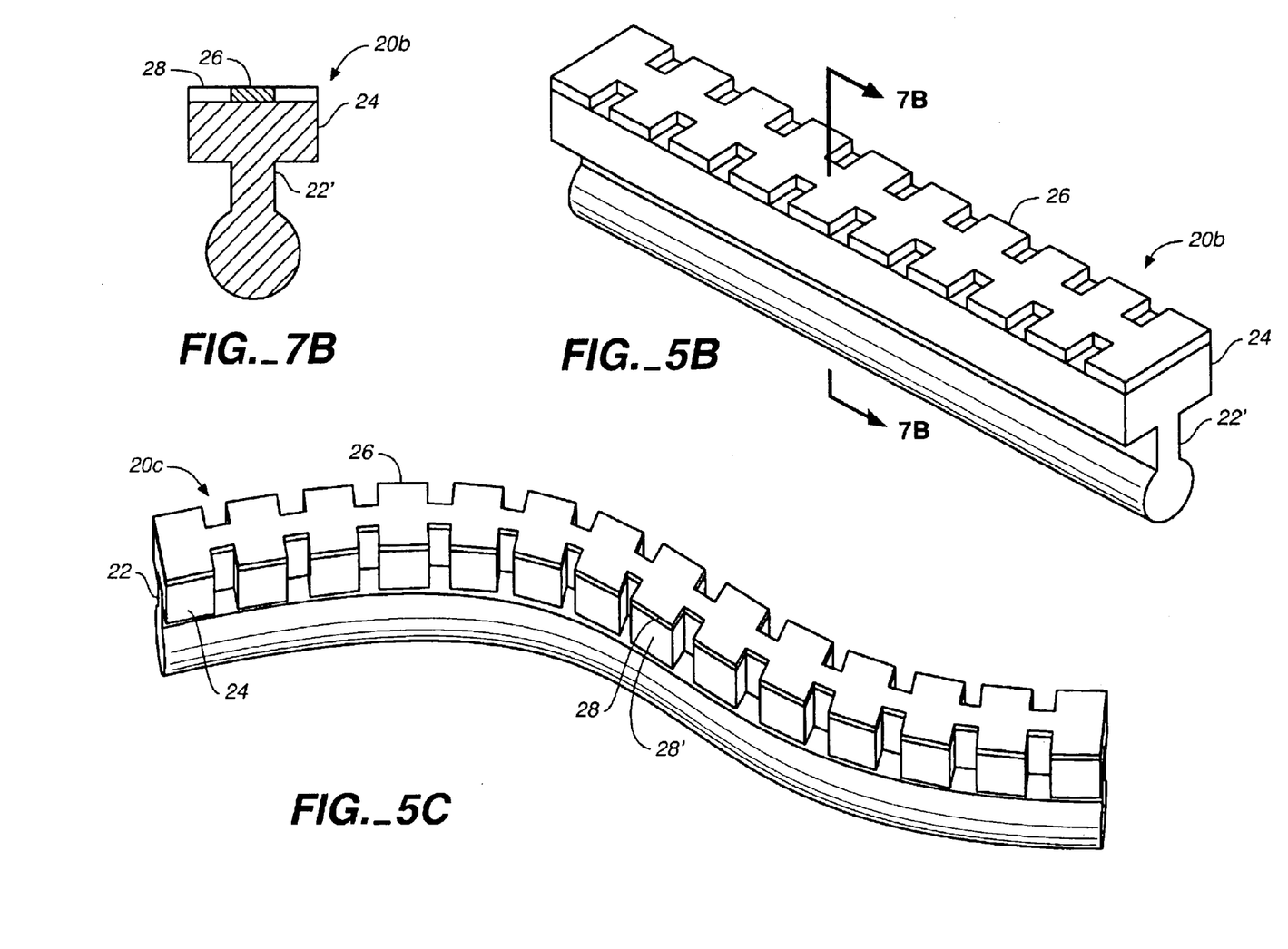
FIG. 5B is a perspective view of a modified version of the insert of FIG. 5A.
FIG. 5C is a perspective view of yet another modified version of the insert of FIG. 5A.
FIG. 7B is a cross-section view of the insert of FIG. 5B taken on a plane designated by line 7B—7B of FIG. 5B.
Figure 6:
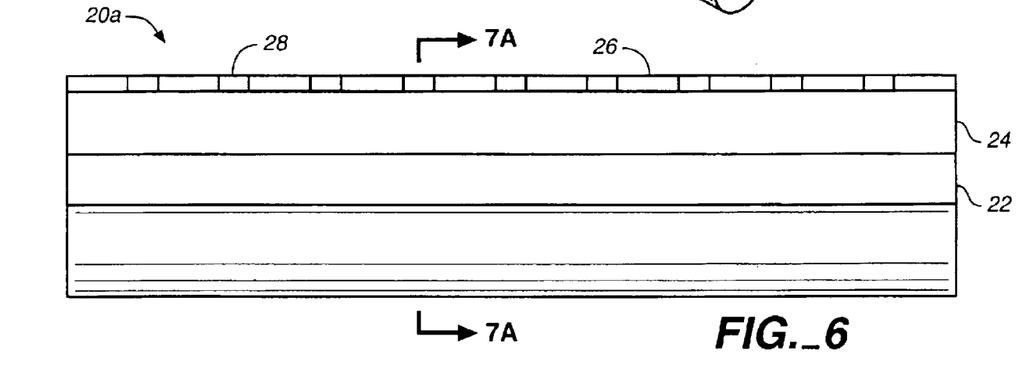
FIG. 6 is a side view of the insert of FIG. 5A.
Figure 7A:
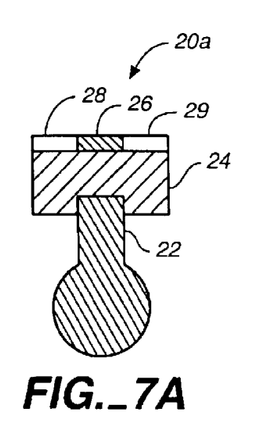
FIG. 7A is a cross-section view of the insert of FIG. 5A taken on a plane designated by line 7A—7A of FIG. 6.

Alternatively, the cushion can be directly secured to a clamp jaw by means described in copending U.S. application Ser. Nos. 09/336,131, 09/491,237 and 09/594,291, filed Jun. 18, 1999, Jan. 25, 2000 and Jun. 15, 2000, respectively, each commonly owned by the assignee of the present application and incorporated herein in their entireties. One such means is depicted in the embodiment of FIGS. 5A, 6 and 7A. Insert 20a includes flexible elongate attachment member 22, which is configured for receipt in an elongate cavity or channel that extends longitudinally of a clamp jaw (not shown). The attachment member 22 includes a securing portion configured to extend through the jaw channel or cavity, thereby securing the cushion to the jaw through an interference fit with the jaw channel or cavity. Such attachment members can be formed of a plastic that is flexible but generally stiffer and less deflectable than the cushion material, such as nylon or polypropylene. Alternatively, attachment member 22' can be integrally formed with cushion 24, as show in insert 20b of FIGS. 5B and 7B. These designs are especially advantageous in that the resultant inserts can accommodate a variety of jaw shapes and configurations, including curved jaws.

Surface overlay 16 is formed of a flexible, non-compliant material. That is, the material must be flexible and capable of bending under an applied load, but at the same time should not deform under such load. A variety of materials known in the art are suitable for use, including metals and relatively hard plastics. Suitable metals include, for example, stainless steel of sufficient thinness to flex or bend under a clamping load, preferably between 0.0002 to 0.004 inches thick. Suitable plastics include, for example, thermoplastics having a 40D–80D shore durometer rating, such as nylon or polypropylene, and preferably having a thickness between 0.005 and 0.015 inches.

Figure 4:
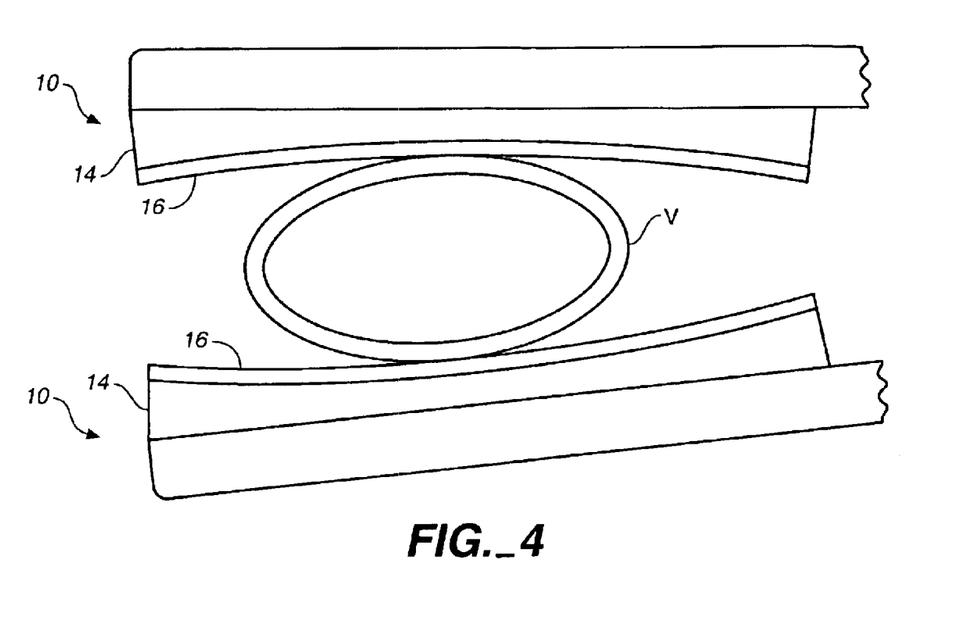
FIG. 4 is a side view of jaw-type surgical clamp, with parts broken away, having the inserts of FIG. 1 installed on the jaws and engaged with a vessel.

The combination of the flexible, non-compliant surface overlay and the underlying compliant cushion provides for an insert that has advantages of both conventional rigid and atraumatic clamps. The non-compliant overlay provides for an engaging surface having the look, feel and clamping characteristics of a traditional rigid clamp, such as a hard metal clamp. However, the underlying compliant cushion will deform upon application of a clamping load, which in turn also allows the overlay to flex in response to the load. The result is that the insert as a whole deflects to accommodate a clamped vessel. This deflection allows for a more atraumatic method of clamping a vessel while at the same time providing for gripping characteristics previously associated only with rigid metal clamps. This deflecting action is illustrated in FIG. 4, which shows vessel V being engaged by clamp jaws containing inserts 10.

FIGS. 5A–7B depict inserts according to a second embodiment of the invention. Insert 20a of FIGS. 5A, 6 and 7A includes compliant cushion 24 and surface overlay 26. The cushion is secured to flexible elongate attachment member 22 as described above. Surface overlay 26 includes a series of notches 28 and 29 that are located along the sides of the overlay. The addition of these notches does not diminish the advantages of the cushion and overlay combination as previously described, but does operate to provide for increased flexibility of the overlay. The increased flexibility is exhibited not only laterally, but also, e.g., in directions perpendicular to the overlay surface, as well as axial to the insert. This increased flexibility allows for an increased ability to bend and twist the insert. This increased flexibility of the overlay, together with the flexible nature of attachment member 22, allows the insert to be more easily installed onto curved jaws of varying configurations. Insert 20b of FIGS. 5B and 7B exhibits similar characteristics, with the exception that attachment member 22' is integrally formed with cushion 24. This increased flexibility of these inserts is illustrated in FIG. 5C which shows insert 20c in a flexed position. The flexibility of insert 20c is further improved by the addition of notches 28' provided in the cushion itself, which correspond to notches 28 in the surface overlay.

The clamping or engaging surface of the surface overlay of the invention can be relatively smooth, as shown, for example, with surface overlay 16. Alternatively, surface overlays according to the invention can be textured with surface irregularities, for example, repeating or random patterns of serrations, bumps, protrusions or other surface irregularities known in the art, in order to provide additional traction with a clamped vessel or engaged tissue. Other methods of providing a surface overlay textured with surface irregularities are also contemplated, including roughening the surface of the overlay, such as by scoring the surface.

Figure 8:
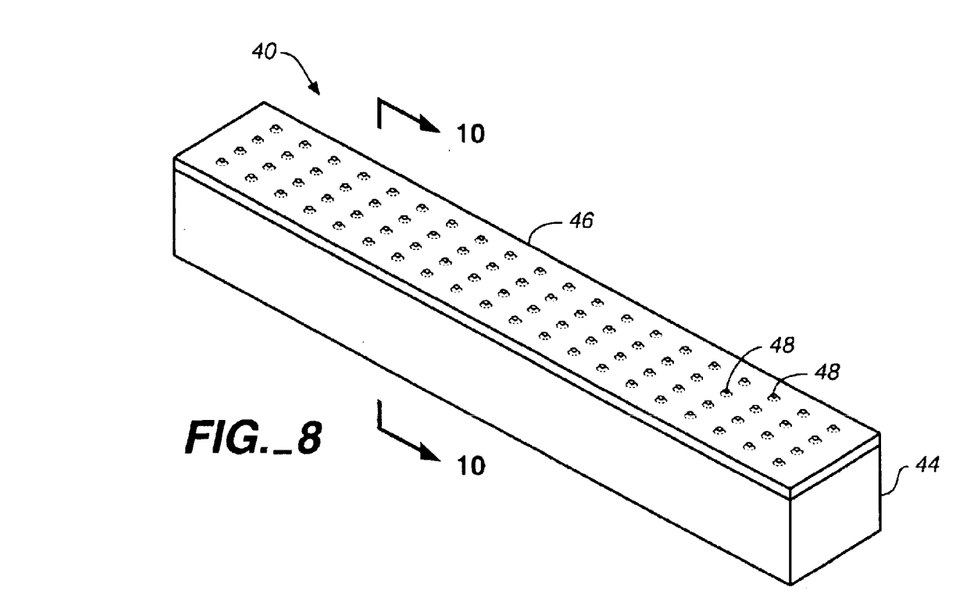
FIG. 8 is a perspective view of an insert according to a third embodiment of the invention.
Figures 9, 10:
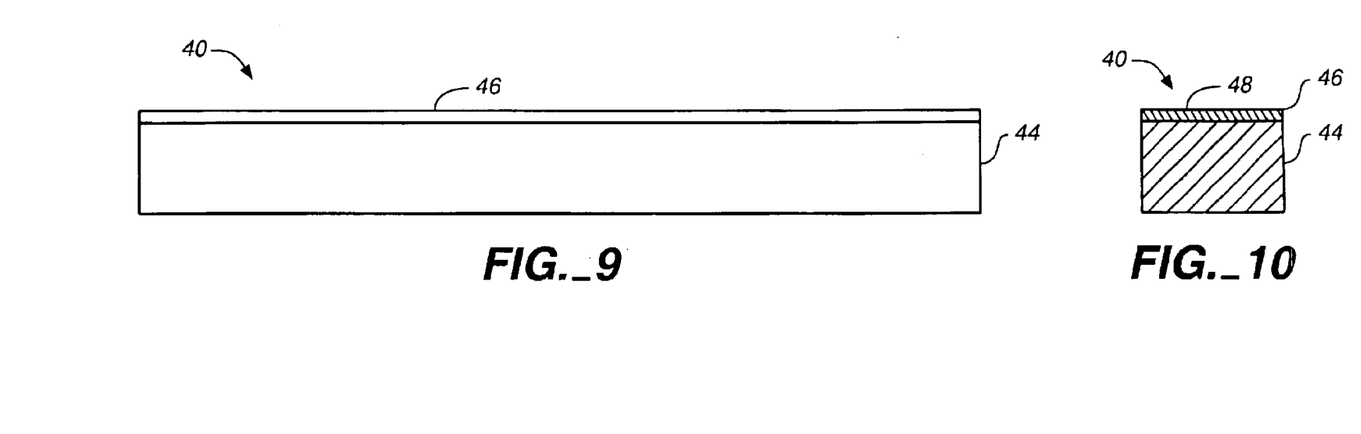
FIG. 9 is a side view of the insert of FIG. 8.
FIG. 10 is a cross-section view of the insert of FIG. 8 taken on a plane designated by line 10—10 of FIG. 9.
Figure 11:
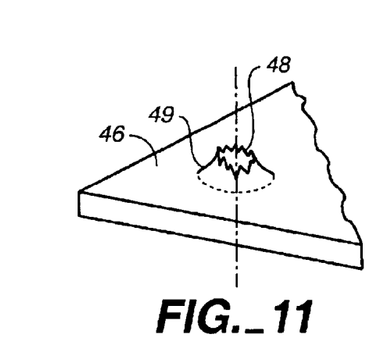
FIG. 11 is an expanded perspective view of the surface overlay of the insert of FIG. 8, with parts broken away.

FIGS. 8–10 depict a third embodiment of the invention having a surface overlay with a tractive surface. Insert 40 includes compliant cushion 44 and surface overlay 46. Overlay 46 is formed of a thin metal, preferably stainless steel, that has been perforated. Each perforation 48 creates a surface irregularity that can increase the traction of the overlay on a clamped vessel or tissue. The perforations can be formed in a variety of ways, including punching or stamping a smooth sheet of metal to form the perforations. In such cases, the resulting punched holes will typically have roughened and irregular edges 49 extending upward from the surface in the direction of the punching action, as is depicted in FIG. 11. Such roughened and irregular hole edges provide for additional traction with an engaged vessel or tissue. The hole edges may be rounded off or otherwise smoothed to achieve the desired gripping-surface without being overly sharp.

Figure 12:
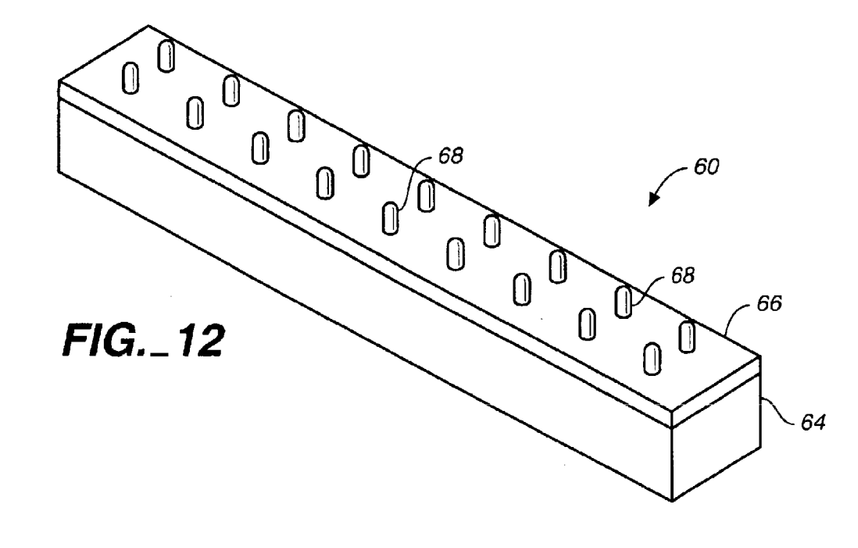
FIG. 12 is a perspective view of an insert according to a fourth embodiment of the invention.
Figure 13:
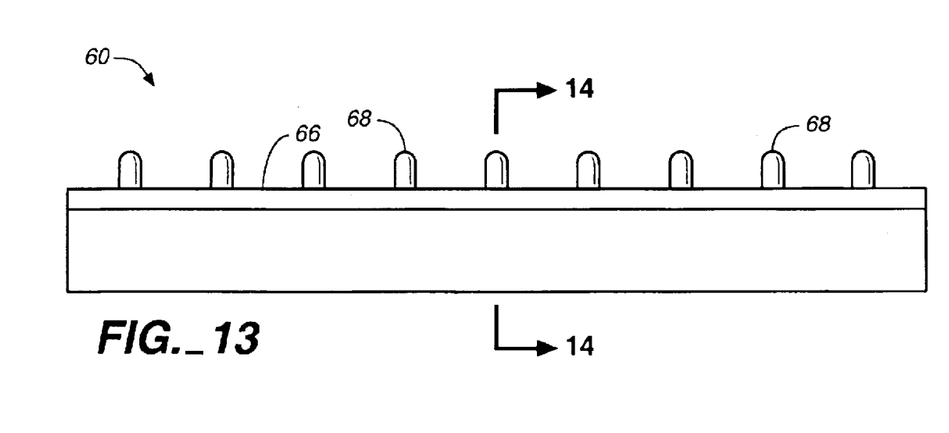
FIG. 13 is a side view of the insert of FIG. 12.
Figure 14:
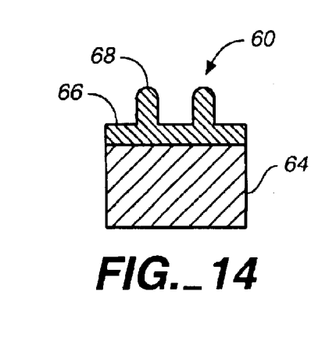
FIG. 14 is a cross-section view of the insert of FIG. 12 taken on a plane designated by line 14—14 of FIG. 13.

FIGS. 12–14 depicts a fourth embodiment of the invention, also having a surface overlay with a tractive surface having surface irregularities. In this embodiment, insert 60 includes cushion 64 and surface overlay 66. Overlay 66 itself includes columns 68 extending upward from the overlay, again for providing additional traction between the insert and a clamped vessel or tissue. The columns extend from the overlay in a direction generally perpendicular to the cushion surface. As illustrated, columns 68 are arranged in two parallel rows, with the columns within each row spaced uniformly, but it will be understood that the invention also contemplates other arrangements of columns, such as opposing, angled or random configurations. Likewise the columns may be of uniform cross-section as shown, or the column cross-sections may vary, providing for a sharper, more pointed protrusive surface.

Inserts according to the present invention can be assembled in ways known in the art. For ease of manufacture, where the compliant cushion is formed of, for example, an elastomeric thermoplastic, and the attachment member is formed of a separate material, it is desirable to employ a process where the attachment member is first provided, and then the compliant cushion is overmolded onto the attachment member. The surface overlay can then be secured onto the cushion surface by a variety of means. If the overlay is also a thermoplastic, the overlay can be subsequently overmolded onto the formed cushion. Alternatively, the overlay can be secured to the cushion surface by other means, such as adhesive bonding or the like. Adhesive bonding is generally more appropriate, for example, where the overlay is a metal. Other methods of assembling the insert according to the invention will be readily apparent to those skilled in the art.

It is to be appreciated that the invention contemplates inserts having any combination of surface overlays and compliant cushions, as described above. Further, any of the surface overlays and/or the cushions themselves can be provided with notches to increase flexibility of the inserts. Also, any of the surface overlay and cushion combinations can be mounted on or formed onto any of the attaching structures described. Although only certain embodiments have been illustrated and described, those having ordinary skill in the art will understand that the invention is not intended to be limited to the specifics of any of these embodiments, but rather is defined by the accompanying claims.

We claim:

1. An insert for attachment to a jaw of a jaw-type occlusion device, comprising:

an attaching structure for attaching the insert to the jaw;

a compliant cushion secured to the attaching structure and having a surface; and a flexible non-compliant surface overlay secured onto the cushion surface for engagement with a vessel or other body tissue, wherein the surface overlay includes a series of notches extending along sides of the overlay to provide for increased flexibility of the overlay.

2. An insert for attachment to a jaw of a jaw-type occlusion device, the jaw having a channel or cavity extending longitudinally therein, the insert comprising:

a compliant cushion having a surface;

a flexible elongate attachment member having a securing portion configured to extend through the jaw channel or cavity; and a flexible non-compliant surface overlay secured onto the cushion surface for engagement with a vessel or other body tissue, wherein the surface overlay includes a series of notches extending along sides of the overlay to provide for increased flexibility of the overlay.

3. An insert for attachment to a jaw of a jaw-type occlusion device, comprising:

an attaching structure for attaching the insert to the jaw;

a compliant cushion secured to the attaching structure and having a surface; and a flexible non-compliant surface overlay secured onto the cushion surface for engagement with a vessel or other body tissue, the overlay being formed of a metal that extends over the entire cushion surface, and wherein the surface overlay further includes a series of notches extending along sides of the overlay to provide for increased flexibility of the overlay.

4. An insert for attachment to a jaw of a jaw-type occlusion device, comprising:

an attaching structure for attaching the insert to the jaw;

a compliant cushion secured to the attaching structure and having a surface; and a flexible non-compliant surface overlay secured onto the cushion surface for engagement with a vessel or other body tissue, the overlay being formed of a thermoplastic and further including a plurality of protrusions extending from the overlay in a direction generally perpendicular to the cushion surface for increased traction with an engaged vessel or body tissue, wherein the surface overlay further includes a series of notches extending along sides of the overlay to provide for increased flexibility of the overlay.

5. An insert for attachment to a jaw of a jaw-type occlusion device, comprising:

a compliant cushion having first and second surfaces, the second surface being adapted for releasable attachment to the jaw; and a flexible non-compliant surface overlay secured onto the first surface of the cushion, the overlay adapted for engagement with a vessel or other body tissue, wherein the surface overlay includes a series of notches extending along sides of the overlay to provide for increased flexibility of the overlay.

6. An insert for attachment to a jaw of a jaw-type occlusion device, comprising:

a attaching structure for attaching the insert to the jaw;

a compliant cushion secured to the attaching structure and having a surface; and a flexible non-compliant surface overlay secured onto the cushion surface for engagement with a vessel or other body tissue, wherein the tissue engaging surface of the surface overlay is formed of a perforated metal.

7. The insert of claim 6 wherein perforations in the metal are formed by punching holes through the metal.

8. An insert for attachment to a jaw of a jaw-type occlusion device, the jaw having a channel or cavity extending longitudinally therein, the insert comprising:

a compliant cushion having a surface;

a flexible elongate attachment member having a securing portion configured to extend through the jaw channel or cavity; and a flexible non-compliant surface overlay secured onto the cushion surface for engagement with a vessel or other body tissue, wherein the tissue engaging surface of the surface overlay is formed of a perforated metal.

9. The insert of claim 8 wherein perforations in the metal are formed by punching holes through the metal.

10. An insert for attachment to a jaw of a jaw-type occlusion device, comprising:

a compliant cushion having first and second surfaces, the second surface being adapted for releasable attachment to the jaw; and a flexible non-compliant surface overlay secured onto the first surface of the cushion, the overlay adapted for engagement with a vessel or other body tissue, wherein the tissue engaging surface of the surface overlay is formed of a perforated metal.

11. An insert for attachment to a jaw of a jaw-type occlusion device, comprising:

a compliant cushion having first and second surfaces, the second surface being adapted for releasable attachment to the jaw; and a flexible non-compliant surface overlay secured onto the first surface of the cushion, the overlay adapted for engagement with a vessel or other body tissue, wherein the tissue engaging surface of the surface overlay is formed of a perforated metal.

12. The insert of claim 11 wherein perforations in the metal are formed by punching holes through the metal.

* * * * *